United States Patent [19]

Bernstein

[11] Patent Number: 4,505,896

[45] Date of Patent: Mar. 19, 1985

[54] METHOD OF TREATING ACNE VULGARIS AND COMPOSITION

[75] Inventor: Joel E. Bernstein, Deerfield, Ill.

[73] Assignee: Elorac, Ltd., Northbrook, Ill.

[21] Appl. No.: 209,649

[22] Filed: Nov. 24, 1980

Related U.S. Application Data

[63] Continuation-in-part of Ser. No. 31,535, Apr. 19, 1979, abandoned.

[51] Int. Cl.$^3$ ............................................. A61K 31/455
[52] U.S. Cl. ...................................... 424/164; 514/24; 514/29; 514/154; 514/161; 514/356
[58] Field of Search ............................... 424/266, 164

[56] References Cited

U.S. PATENT DOCUMENTS 3,636,202  1/1972  Klein ................................. 424/183

FOREIGN PATENT DOCUMENTS 964444  7/1964  United Kingdom .

OTHER PUBLICATIONS

Chemical Abstracts, 69: P98648u, (1968).
Chemical Abstracts, 74: 146403h, (1971).
Chemical Abstracts, 83: P32922g, (1975).
Chemical Abstracts, 74: 40869z, (1971).
Chemical Abstracts, 82: 231u, (1975).

*Primary Examiner*—Leonard Schenkman
*Attorney, Agent, or Firm*—Ronald A. Sandler; Jerry A. Schulman

[57] ABSTRACT

An improved method of treating acne vulgaris comprising administering a therapeutically effective amount of nicotinic acid or nicotinamide and compositions useful in said method.

25 Claims, No Drawings

METHOD OF TREATING ACNE VULGARIS AND COMPOSITION

RELATED APPLICATION

This is a continuation-in-part of my copending application Ser. No. 31,535, filed Apr. 19, 1979, now abandoned.

BACKGROUND OF THE INVENTION

Acne vulgaris is an inflammatory disease of the sebaceous glands characterized by an eruption of the skin, often pustular in nature but not suppurative. Acne is a common affliction of the adolescent and affects a small but significant percentage of the adult population. Acne involvement results in unsightly lesions, particularly on the face, and in some cases results in severe scarring.

There are a variety of methods for treating acne vulgaris including topically applying various scrubbing or abrasive compositions, topically applying deep cleaning or astringent compositions and also applying ultraviolet radiation. Nevertheless, acne vulgaris is seldom cured and only can be contained with difficulty.

Nicotinic acid and nicotinamide, water soluble vitamins, whose physiological active forms nicotinamide adenine dinucleotide (NAD) and nicotinamide adenine dinucleotide phosphate (NADP) serve a vital role as coenzymes in a variety of important metabolic reactions. Nicotinic acid is an essential dietary constituent, the lack of which leads to pellagra, a condition characterized by an erythematous skin eruption as well as gastrointestinal and neurological symptoms. Nicotinic acid and nicotinamide have been used routinely to treat pellagra for which they are therapeutic.

Nicotinic acid as well as nicotinamide are available from a variety of pharmaceutical houses such as Armor Pharmaceutical Company located in Phoenix, Ariz.; Brown Pharmaceutical Company Inc. located in Los Angeles, Calif.; and Keith Pharmaceutical Inc. located in Miami, Fla.

Although the above noted uses for nicotinic acid and nicotinamide are well documented, in addition, these vitamins have been used unsuccessfully in treatment of schizophrenia and atherosclerotic heart disease.

I have found surprisingly that nicotinic acid and nicotinamide are useful in the treatment of acne vulgaris by administering a therapeutically amount either topically or orally; I have also found that combinations of nicotinic acid and nicotinamide with certain chemical agents known to be effective in treating acne are more effective in treating acne than would be expected by treatment with the individual agents themselves. Such formulations include combinations of nicotinic acid or nicotinamide and sulfur, salicylic acid, benzoyl peroxide, vitamin A acid, erythromycin base, clindamycin phosphate and tetracycline hydrochloride.

SUMMARY

The present invention provides an improved method of and composition for the treatment of acne vulgaris involving the periodic application of an effective amount of nicotinic acid or nicotinamide or combination thereof with sulfur, salycylic acid, benzoyl peroxide, vitamin A, acid, erythromycin base, clindamycin phosphate and tetracycline hydrochloride.

DETAILED DESCRIPTION OF PREFERRED EMBODIMENTS

In the practice of this invention, nicotinic acid or nicotinamide is administered orally in doses of 100 to 600 milligrams (mg) per day in divided doses taken 2 to 4 times per day. Also useful are topical solutions of nicotinamide and nicotinic acid in various organic vehicles such as a combination of ethyl alcohol and propylene glycol in which the active ingredient is present in the range of from about 1% to about 7% by volume of the carrier.

Additionally topical solutions of nicotinic acid or nicotinamide in various organic carriers in concentrations ranging ffrom 1 to 10% by volume of the carrier are incorporated into various organic vehicles including solutions, lotions, creams, gels, and ointments along with one or more of the following ingredients: sulfur in concentrations of 0.5% to 10% by volume; salicylic acid in concentrations of 0.5% to 10% by volume; benzoyl peroxide in concentrations of 5 to 10% by volume; vitamin A acid in concentrations from 0.01% to 0.5% by volume; erthromycin base in concentrations of from 1 to 5% by volume; clindamycin phosphate in concentrations from 1-5% by volume; tetracycline hydrochloride in concentrations from 1-5% by volume.

These applications, at least twice daily, resulted in a substantial and beneficial effect, that is a decrease in the inflammatory lesions such as papules, pustules, cysts but not comedones within approximately two weeks. The following examples illustrate the present invention.

EXAMPLE 1

100 milligrams of Nicotinic acid, obtained from the Armor Pharmaceutical Company, was orally administered to a 180 pound, 23 years old, male patient suffering from acne vulgaris. This patient received 3 oral doses of 100 milligrams of nicotinic acid 5-6 hours apart. These daily doses were required over a period of 14 days to observe a beneficial effect of a decrease in the inflammatory lesions.

EXAMPLE 2

100 milligrams of Nicotinamide, obtained from the Armor Pharmaceutical Company, was orally administered to a 120 pound, 21 years old, female patient suffering from acne vulgaris. This patient received 3 oral doses of 100 milligrams of nicotinamide, 5-6 hours apart. These daily doses were required over a period of 14 days to effect a decrease in inflammatory lesions.

EXAMPLE 3

600 milligrams of Nicotinic Acid, obtained from the Armor Pharmaceutical Company, was orally administered to a 160 pound, 24 year old, male patient suffering from acne vulgaris. This patient received 3 repeated doses, each being 200 milligrams of nicotinic acid, 5-6 hours apart. The daily dosage was repeated for 14 days before a decrease in the inflammatory lesions was noted.

EXAMPLE 4

600 milligrams of Nicotinamide, obtained from the Armor Pharmaceutical Company, was orally administered to a 160 pound, 28 years old, male patient suffering from acne vulgaris. This patient received 3 doses per day, each of 200 milligrams of nicotinamide, 5 hours apart. The daily dosage was repeated for 28 days before a decrease in the inflammatory lesions was noted.

EXAMPLE 5

Nicotinamide obtained from the Armor Pharmaceutical Comany was prepared with an ethyl alcohol carrier to form a 2% by volume solution of nicotinamide in alcohol. Twice daily topical treatments were administered to a 115 pound, 22 years old, female patient suffering from acne vulgaris. The topical treatments were administered 12-14 hours apart and this daily routine was repeated for a period of 14 days before a noticeable decrease in the inflammatory lesions occured.

EXAMPLE 6

A 5% by volume solution of nicotinamide in a 70% ethyl alcohol and 30% propylene glycol carrier was prepared. This solution was topically administered twice daily to a 170 pound, 24 years old, male patient suffering from acne vulgaris. The patient received topical treatments 12-14 hours apart and the daily treatments were repeated for 14 days before a noticeable reduction in the inflammatory lesions occured.

EXAMPLE 7

A 2% solution of nicotinic acid in an alcohol carrier was prepared. Twice daily topical applications were administered to a 150 pound, 27 years old, male patient suffering from acne vulgaris. The topical treatments were administered 12-14 hours apart and 28 days of treatment were required before a noticeable reduction in the inflammatory lesions occured.

EXAMPLE 8

A 5% solution of nicotinic acid in an alcohol-glycol carrier was prepared. Twice daily topical treatments of this solution were administered to a 118 pound, 24 years old, female patient suffering from acne vulgaris. The patient received two treatments 12-14 hours apart for a period of 14 days before a noticeable reduction in the inflammatory lesions occured.

The following examples illustrate a variety of combinations of nicotinamide and nicotinic acid with other chemical agents known to be effective against acne vulgaris. I have utilized these combinations in potassium-iodide-induced inflammation of the skin, a model that closely simulates acne vulgaris.

EXAMPLE 9

Solutions containing 1%, 5%, and 10% nicotinamide or nicotinic acid, acid, and 0.5%, 2%, 5%, and 10% sulfur were prepared in 2 vehicles, 1 containing 70% ethanol and 30% propylene glycol and the other containing 60% ethanol, 10% propylene glycol and 1% laureth—4. The solutions were applied to small areas on the backs of 10 normal volunteers aged 21-30 years and after drying patches containing 40% potassium-iodide (KI) were applied. Control patches had only the vehicle alone applied. The patches were read 48 hours after application. All combinations of nicotinamide or nicotinic acid with sulfer were dramatically effective at blocking the acneform papules and pustules which developed in the control areas.

EXAMPLE 10

Vehicles containing 1%, 5%, and 10% nicotinamide and 0.5%, 2%, 6% and 10% salicylic acid were prepared and applied on the backs of 10 volunteers in order to evaluate suppression of KI-induced acne form lesions. The vehicles included a gel containing 60% propylene glycol, 19.4% ethyl alcohol, hydroxypropyl cellulose and water, and a solution containing 70% ethyl alcohol and 30% propylene Glycol. All combinations of nicotinamide and salicylic acid suppressed acne lesions in the test areas, with suppression being complete in the combinations containing more than 2% salicylic acid.

EXAMPLE 11

1,2,5, and 10% concentrations by volume of nicotinic acid and nicotinamide were incorporated into gels containing 5% and 10% concentrations of benzoyl peroxide. These gels also contained 37% ethanol, 6% laureth—4, carbomer 940, di-isopropanolamine, disodium edetate and water. These gels were applied to the backs of 20 volunteers and acneform eruptions were induced in the test areas with KI and 10% crude coal tar under occlusion. Combinations of the nicotinic acid or nicotinamide and benzoyl peroxide were quite effective in suppressing the resulting "acne", and the combination products were especially active in the coal tar assay.

EXAMPLE 12

2% and 5% concentrations of nicotinamide were incorporated into gel and cream vehicles containing 0.025%, 0.05% or 0.1% by volume vitamin A acid and tested in the previously described inflammatory acne models and compared to vehicle controls. The combinations offered impressive suppression of KI and coal tar acnegenesis.

EXAMPLE 13

Solutions containing 70% ethanol, 30% propylene glycol were utilized as the vehicles for a series of acne treatment preparations containing 1%, 2%, 5%, and 10% concentrations by volume of nicotinic acid or nicotinamide and 1%, 2%, and 5% concentrations by volume of erythromycin base. Such combination formulations were dramatically effective at surpressing KI induced inflammation, although less potent against coal tar induced acnegenesis.

EXAMPLE 14

Ointments of white petrolatum were prepared containing 1%, 2%, 5% and 10% concentrations of nicotinic acid or nicotinamide combined with 1-5% concentrations of clindamycin phosphate by volume and applied to subjects' backs after induction of acneform papules and pustules with KI. These acne lesions cleared within 4 days with such treatment.

EXAMPLE 15

Tetracycline hydrochloride, in concentrations by volume of 1,2, and 5%, was incorporated in creams containing 1%, 2%, 5%, and 10% nicotinamide and applied to subjects' backs after induction of papules and pustules by KI. Acne lesions cleared within 5 days. However, a slight yellow staining of the skin was noted in the treatment areas.

EXAMPLE 16

A solution containing 70% ethanol and 30% propylene glycol was utilized to prepare acne treatment preparations containing 1%, 2%, 5% and 10% nicotinamide and combinations of sulfur and salicylic acid by volume as follows: 0.5% sulfur, 2% salicylic acid; 2% sulfur, 2% salicylic acid; 5% sulfur, 5% salicylic acid. These solutions were utilized in suppressing KI-induced inflammation and provided slightly superior acne suppressive effects than the combination of just nicotinamide and sulfur or nicotinamide and salicylic acid.

The present invention includes within the scope thereof pharmaceutical compositions suitable for both topical and oral administration having as an active ingredient thereof nicotinic acid or nicotinamide. Also included in the scope of the invention is the combination of nicotinic acid or nicotinamide with one or more of sulfur, salicylic acid, benzoyl peroxide, vitamin A acid, erythromycin base, clindamycin phosphate and tetracycline hydrochloride. Where appropriate a pharmaceutically acceptable carrier or diluent is employed.

Solid dosage froms for oral administration where applicable include capsules, tablets, pills, powders and granules. In such dosage forms, the active compound is admixed with at least one inert diluent such as sucrose, lactrose or starch. Such dosage forms can also comprise, as is normal practice, additional substances other than inert diluents, e.g. lubricating agents such as magnesium stearate. In the case of capsules, granules, tablets and pills, the dosage forms may also comprise buffering agents. Tablets and pills can additionally be prepared with enteric codings, if desired.

Liquid dosage forms for oral administration where applicable include pharmaceutically acceptable emulsions, solutions, suspensions, syrups, and elixirs containing inert diluents commonly used in the art, such as water. Besides such inert diluents, compositions can also include adjuvants such as wetting agents, emulsifying agents, suspending agents, sweetening, flavoring and performing agents.

Liquid dosage forms for topical administration includes acceptable emulsions, solutions and suspensions containing volatile diluents commonly used in the art, such as alcohol, glycol and the like. Beside such diluents, topically applied compositions may also include wetting agents, emulsifying and suspending agents.

It will be apparent to those skilled in the art that only the preferred embodiments have been described by way of exemplification and that there are various modifications and alterations therein which fall in the scope of this invention and are intended to be covered by the claims appended hereto.

What is claimed is:

1. A method of decreasing the inflammatory lesions of acne vulgaris in human patients having such inflammatory lesions, said method comprising administering a therapeutically effective amount of nicotinamide to a patient having such inflammatory lesions.

2. The method of claim 1, wherein said administration is topical with the effective ingredient being dispersed in a pharmaceutically acceptable carrier.

3. The method of claim 2, wherein the effective ingredient is nicotinamide present in the amount of not less than about 1% by volume.

4. The method of claim 2, wherein the effective ingredient is nicotinamide present in the range of between about 1% and about 7% by volume.

5. The method of claim 2, wherein the carrier is selected from an alcohol or a glycol or mixtures thereof.

6. The method of claim 1, wherein administration is by the oral route.

7. The method of claim 6, wherein the effective ingredient is present in an amount in the range of between 100 mg. and 600 mg. per day administered in divided doses.

8. A method of decreasing the inflammatory lesions of acne vulgaris in human patients having such inflammatory lesions, said method comprising topically administering a therapeutically effective amount of nicotinamide in combination with one or more of sulfur, salicylic acid, benzoyl peroxide, vitamin A acid, erythromycin base, clindamycin phosphate and tetracycline hydrochloride to a patient having such inflammatory lesions.

9. The method fo claim 8, wherein the effective ingredient is dispersed in a pharmaceutically acceptable carrier.

10. The method of claim 9 wherein the effective ingredient includes sulfur present in the range of from about 0.5% to about 10% by volume.

11. The method of claim 9 wherein the effective ingredient includes salicylic acid present in the range of from about 0.5% to about 10% by volume.

12. The method of claim 9 wherein the effective ingredient includes benzoyl peroxide present in the range of from about 5% to about 10% by volume.

13. The method of claim 9 wherein the effective ingredient includes vitamin A acid present in the range of from about 0.01% to about 0.5% by volume.

14. The method of claim 9 wherein the effective ingredient includes erythromycin base present in the range of from about 1% to about 5% by volume.

15. The method of claim 9 wherein the effective ingredient includes clindamycin phosphate present in the range of from about 1% to about 5% by volume.

16. The method of claim 9 wherein the effective ingredient includes tetracycline hydrochloride present in the range of from about 1% to about 5% by volume.

17. A topical composition effective in decreasing the inflammatory lesions of acne vulgaris in human patients having such inflammatory lesions, comprising a pharmaceutically acceptable carrier containing a therapeutically effective amount of nicotinamide in combination with a therapeutically effective amount of one or more of sulfur, salicylic acid, benzoyl peroxide, vitamin A acid, erythromycin base, clindamycin phosphate, and tetracycline hydrochloride.

18. The composition of claim 17 wherein the effective ingredient includes nicotinamide present in an amount not less than about 1% by volume.

19. The composition of claim 17 wherein the effective ingredient includes sulfur present in the range of from 0.5% to about 10% by volume.

20. The composition of claim 17 wherein the effective ingredient includes salicylic acid present in the range of from about 0.5% to about 10% by volume.

21. The composition of claim 17 wherein the effective ingredient includes benzoyl peroxide present in the range of from about 5% to about 10% by volume.

22. The composition of claim 17 wherein the effective ingredient includes vitamin A acid present in the range of from about 0.01% to about 0.5% by volume.

23. The composition of claim 17 wherein the effective ingredient includes erythromycin base present in the range of from about 1% to about 5% by volume.

24. The composition of claim 17 wherein the effective ingredient includes clindamycin phosphate present in the range of from about 1% to about 5% by volume.

25. The compostion of claim 17 wherein the effective ingredient includes tetracycline hydrochloride present in the range of from about 1% to about 5% by volume.

* * * * *